US012611186B2

(12) United States Patent 
Aono

(10) Patent No.: US 12,611,186 B2 
(45) Date of Patent: Apr. 28, 2026

(54) ULTRASOUND IMAGE PROCESSING DEVICE FORMING ULTRASOUND IMAGE BASED ON RF SIGNALS SUBJECTED TO SIGNAL PROCESSING IN CONSIDERATION OF TARGET REGION

(71) Applicant: FUJIFILM Healthcare Corporation, Chiba (JP)

(72) Inventor: Shohei Aono, Chiba (JP)

(73) Assignee: FUJIFILM Corporation, Tokyo (JP)

(*) Notice: Subject to any disclaimer, the term of this patent is extended or adjusted under 35 U.S.C. 154(b) by 119 days.

(21) Appl. No.: 18/520,459

(22) Filed: Nov. 27, 2023

(65) Prior Publication Data

US 2024/0180528 A1 Jun. 6, 2024

(30) Foreign Application Priority Data

Dec. 5, 2022 (JP) ................................. 2022-194176

(51) Int. Cl. 
*A61B 8/00* (2006.01)

(52) U.S. Cl. 
CPC .............. *A61B 8/5207* (2013.01); *A61B 8/58* (2013.01)

(58) Field of Classification Search 
CPC ......................... A61B 8/5253; G01S 15/8995 
See application file for complete search history.

(56) References Cited

U.S. PATENT DOCUMENTS

| 6,554,770 | B1* | 4/2003 | Sumanaweera | ......... G06T 3/147 |
| | | | | 600/443 |
| 2007/0014445 | A1* | 1/2007 | Lin | ......................... G03B 42/06 |
| | | | | 382/128 |
| 2010/0331693 | A1* | 12/2010 | Matsunaga | ............ A61B 8/488 |
| | | | | 600/443 |
| 2014/0031687 | A1* | 1/2014 | Kurita | ...................... A61B 8/54 |
| | | | | 600/440 |
| 2014/0187950 | A1* | 7/2014 | Torp | ....................... A61B 8/466 |
| | | | | 600/445 |
| 2016/0103221 | A1* | 4/2016 | Oh | ....................... G01S 7/52073 |
| | | | | 73/628 |
| 2016/0206291 | A1* | 7/2016 | Yang | .................... A61B 8/5253 |
| 2016/0367221 | A1* | 12/2016 | Igarashi | ............... A61B 8/5207 |

(Continued)

FOREIGN PATENT DOCUMENTS

| JP | 2011217927 | 11/2011 |
| JP | 2017012599 | 1/2017 |

(Continued)

*Primary Examiner* — Nyrobi Celestine 
(74) *Attorney, Agent, or Firm* — JCIPRNET

(57) ABSTRACT

An information processing unit executes processing of determining a state of an ultrasound probe based on image data acquired by an ultrasound probe, processing of starting an acquisition of synthesis image data by the ultrasound probe according to the state of the ultrasound probe and ending the acquisition of the synthesis image data according to the state of the ultrasound probe, and processing of synthesizing pieces of synthesis image data sequentially acquired over time to generate panoramic image data. The information processing unit starts the acquisition of the synthesis image data in a case where it is determined that the ultrasound probe is in a stationary state, and ends the acquisition of the synthesis image data in a case where it is determined that the ultrasound probe is in a non-transport state.

6 Claims, 7 Drawing Sheets

(56) References Cited

U.S. PATENT DOCUMENTS

| | | | | |
|---|---|---|---|---|
| 2018/0049721 A1* | 2/2018 | Ben-Lavi | .................. | G06T 7/12 |
| 2019/0216439 A1* | 7/2019 | Somphone | .......... | G01S 7/52065 |
| 2019/0388063 A1 | 12/2019 | Oka et al. | | |
| 2020/0411165 A1* | 12/2020 | Torii | ....................... | G06T 11/60 |
| 2021/0212668 A1* | 7/2021 | Li | ........................... | G01S 17/66 |

FOREIGN PATENT DOCUMENTS

| | | |
|---|---|---|
| JP | 2019217018 | 12/2019 |
| WO | 2014112242 | 7/2014 |

* cited by examiner

Figure 6:
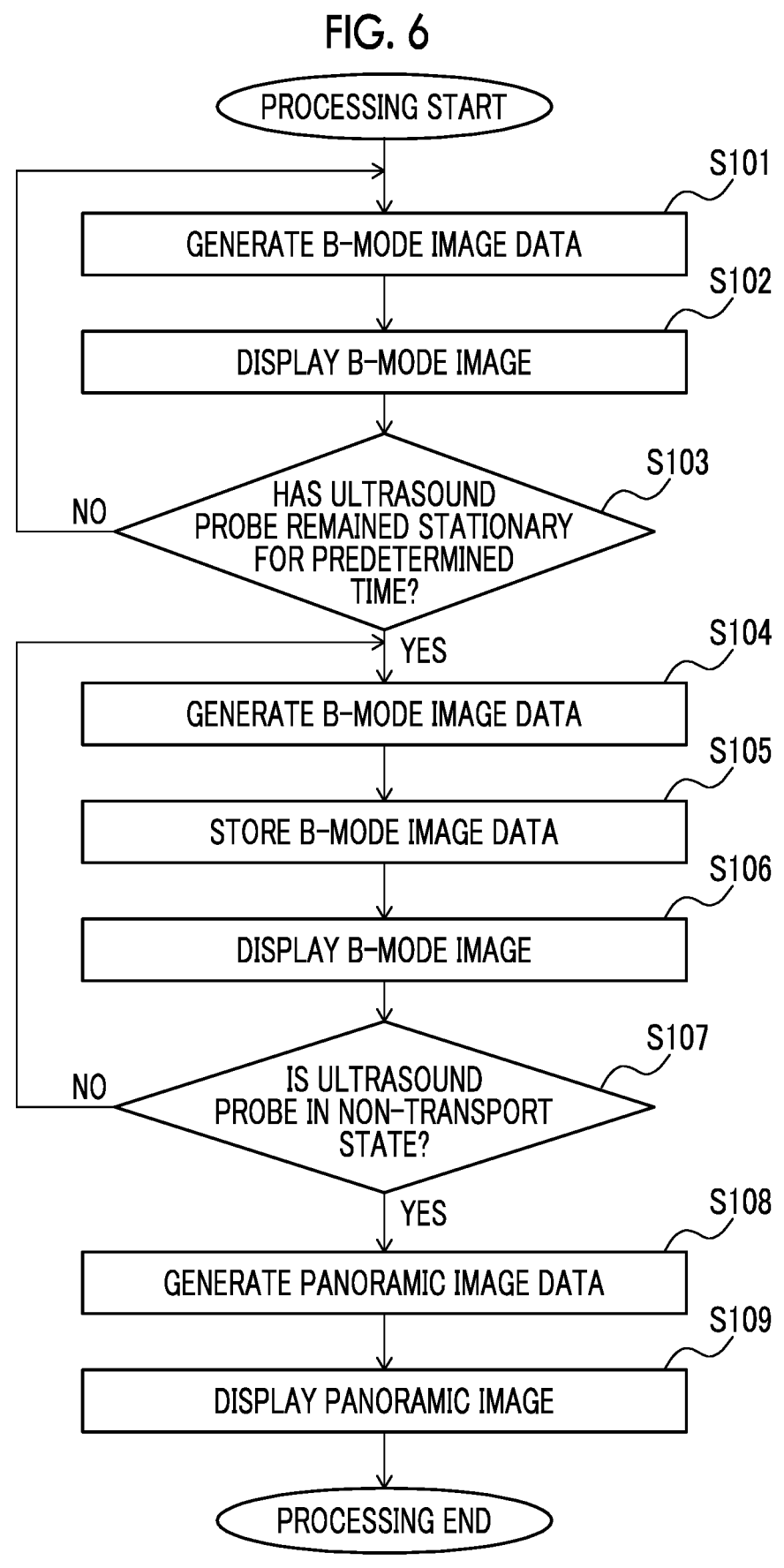

```
            ( PROCESSING START )

│
                    ▼
        ┌─────────────────────────────┐  S101
        │  GENERATE B-MODE IMAGE DATA │
        └─────────────────────────────┘
                    │
                    ▼
        ┌─────────────────────────────┐  S102
        │     DISPLAY B-MODE IMAGE    │
        └─────────────────────────────┘
                    │
                    ▼
              HAS ULTRASOUND            S103
        NO   PROBE REMAINED STATIONARY
             FOR PREDETERMINED
                   TIME?
                    │ YES
                    ▼
        ┌─────────────────────────────┐  S104
        │  GENERATE B-MODE IMAGE DATA │
        └─────────────────────────────┘
                    │
                    ▼
        ┌─────────────────────────────┐  S105
        │    STORE B-MODE IMAGE DATA  │
        └─────────────────────────────┘
                    │
                    ▼
        ┌─────────────────────────────┐  S106
        │     DISPLAY B-MODE IMAGE    │
        └─────────────────────────────┘
                    │
                    ▼
              IS ULTRASOUND             S107
        NO   PROBE IN NON-TRANSPORT
                  STATE?
                    │ YES
                    ▼
        ┌─────────────────────────────┐  S108
        │  GENERATE PANORAMIC IMAGE DATA │
        └─────────────────────────────┘
                    │
                    ▼
        ┌─────────────────────────────┐  S109
        │    DISPLAY PANORAMIC IMAGE  │
        └─────────────────────────────┘
                    │
                    ▼
            ( PROCESSING END )
```

ULTRASOUND IMAGE PROCESSING DEVICE FORMING ULTRASOUND IMAGE BASED ON RF SIGNALS SUBJECTED TO SIGNAL PROCESSING IN CONSIDERATION OF TARGET REGION

CROSS-REFERENCE TO RELATED APPLICATION

This application claims the priority benefits of Japanese application no. 2022-194176, filed on Dec. 5, 2022. The entirety of the above-mentioned patent application is hereby incorporated by reference herein and made a part of this specification.

BACKGROUND

1. Technical Field

The present disclosure relates to an ultrasound image processing device, and particularly, to a device that synthesizes a plurality of images.

2. Description of the Related Art

An ultrasound diagnostic apparatus that acquires an ultrasound image of a subject by transmitting and receiving ultrasound waves to and from the subject using an ultrasound probe is widely used. Regarding the ultrasound diagnostic apparatus, there is a technique for acquiring a plurality of frames of pieces of ultrasound image data while manually moving the ultrasound probe, and stitching a plurality of ultrasound images represented by the plurality of frames of pieces of ultrasound image data to generate a panoramic image. In addition, there is a technique for controlling the ultrasound diagnostic apparatus according to a movement or a state of the ultrasound probe.

JP2019-217018A and JP2011-217927A describe techniques for generating a panoramic image. JP2017-12599A and WO2014/112242A1 describe techniques for controlling an ultrasound diagnostic apparatus according to a movement or a state of an ultrasound probe.

SUMMARY

Some conventional ultrasound diagnostic apparatuses require an operation of a button or the like in acquiring a panoramic image. In this case, the operation for acquiring the panoramic image may become complicated. In addition, in the conventional ultrasound diagnostic apparatus, a transport direction of an ultrasound probe may be shifted during acquiring the panoramic image, which may make it difficult to stitch a plurality of ultrasound images.

An object of the present disclosure is to facilitate an operation for acquiring a panoramic image and processing of generating the panoramic image in an ultrasound image processing device.

According to an aspect of the present disclosure, there is provided an ultrasound image processing device configured to execute: processing of determining a state of an ultrasound probe based on image data acquired by the ultrasound probe; processing of starting an acquisition of synthesis image data by the ultrasound probe according to the state of the ultrasound probe and ending the acquisition of the synthesis image data according to the state of the ultrasound probe; and processing of synthesizing pieces of synthesis image data sequentially acquired over time to generate panoramic image data.

In one embodiment, the processing of generating the panoramic image data includes processing of sequentially updating the panoramic image data each time a predetermined number of frames of pieces of synthesis image data are acquired, and the ultrasound image processing device is configured to further execute processing of sequentially displaying panoramic images based on the updated panoramic image data.

In one embodiment, the acquisition of the synthesis image data is started in a case where it is determined that the ultrasound probe is in a stationary state, and the acquisition of the synthesis image data is ended in a case where it is determined that the ultrasound probe is in a non-transport state.

In one embodiment, the panoramic image data represents, for an overlapping portion of an image represented by the synthesis image data acquired earlier and an image represented by the synthesis image data acquired later, either an image based on the synthesis image data acquired earlier or an image based on the synthesis image data acquired later.

In one embodiment, the processing of generating the panoramic image data includes processing of disposing, within an overlapping portion of two ultrasound images represented by pieces of synthesis image data acquired adjacently on a time axis, a gap image with a predetermined aspect in transition regions of the two ultrasound images.

In one embodiment, the processing of generating the panoramic image data includes processing of disposing, within an overlapping portion of two ultrasound images represented by pieces of synthesis image data acquired adjacently on a time axis, a transparent image that allows one to see through the other in transition regions of the two ultrasound images.

In one embodiment, the processing of generating the panoramic image data includes processing of obtaining, within an overlapping portion of two ultrasound images represented by pieces of synthesis image data acquired adjacently on a time axis, an approximation degree for transition regions of the two ultrasound images, and processing of executing either one of processing of disposing a gap image with a predetermined aspect in the transition regions or processing of disposing a transparent image that allows one to see through the other in the transition regions, according to the approximation degree.

According to the aspect of the present disclosure, it is possible to facilitate an operation for acquiring a panoramic image and processing of generating the panoramic image.

BRIEF DESCRIPTION OF THE DRAWINGS

FIG. 1 is a diagram showing a configuration of an ultrasound diagnostic apparatus according to an embodiment of the present disclosure.

FIG. 2 is a diagram conceptually showing a B-mode image acquired by panoramic image processing.

FIG. 3 is a diagram showing a panoramic image acquired for a region of interest.

FIG. 4 is a diagram showing two region-of-interest images and a boundary image disposed in these transition regions.

FIG. 6 is a flowchart showing a first example of the panoramic image processing.

DESCRIPTION OF THE EMBODIMENTS

Figure 1:
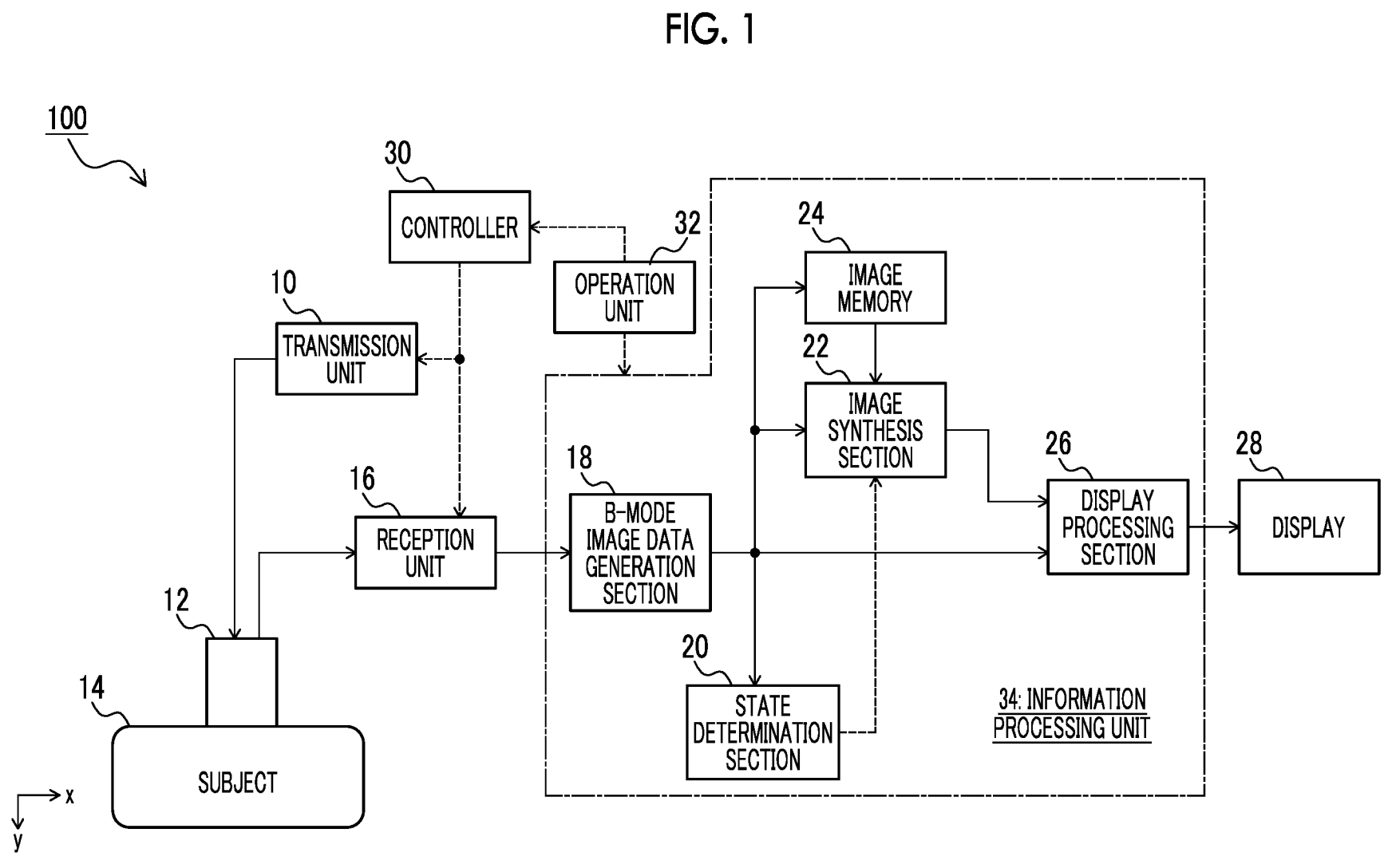
Figure 5:
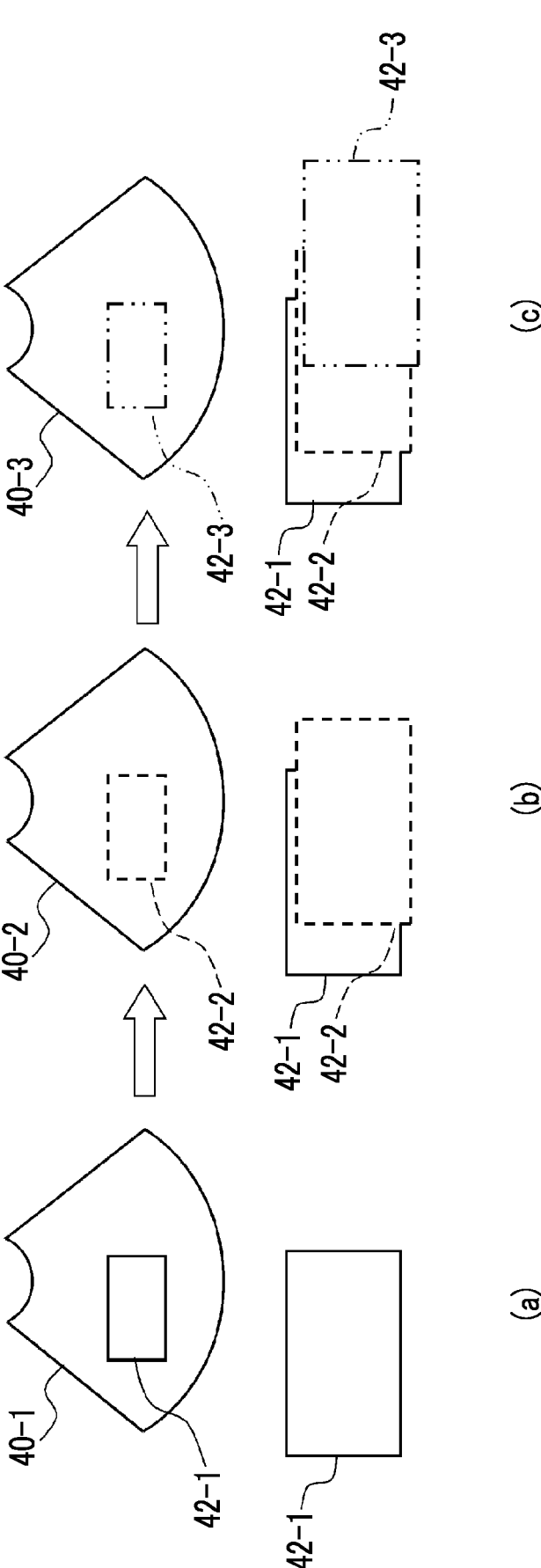
FIG. 5 is a diagram showing an example of an image displayed through real-time panoramic image generation processing.

An embodiment of the present disclosure will be described with reference to each drawing. The same components shown in a plurality of drawings are designated by the same reference numerals, and the description thereof will be omitted. FIG. 1 shows a configuration of an ultrasound diagnostic apparatus 100 according to an embodiment of the present disclosure. The ultrasound diagnostic apparatus 100 comprises a transmission unit 10, an ultrasound probe 12, a reception unit 16, an information processing unit 34, a display 28, a controller 30, and an operation unit 32.

The operation unit 32 may comprise a button, a lever, a keyboard, a mouse, and the like. The operation unit 32 may be a touch panel provided on the display 28. The controller 30 performs overall control of the ultrasound diagnostic apparatus 100 in response to an operation of the operation unit 32 by the user.

The ultrasound probe 12 comprises a plurality of transducer elements. The transmission unit 10 outputs a transmission signal to each transducer element. Each transducer element converts the transmission signal into an ultrasound wave and transmits the ultrasound wave to a subject 14. The transmission unit 10 adjusts a delay time of the transmission signal to be output to each transducer element such that the ultrasound waves emitted from each transducer element are intensified in a specific direction. As a result, a transmission beam by the ultrasound wave is formed in the specific direction. The transmission unit 10 changes the delay time of the transmission signal to be output to each transducer element and scans the subject 14 with the transmission beam.

Each of the plurality of transducer elements receives the ultrasound wave reflected by the subject 14, converts the received ultrasound wave into an electrical signal, and outputs the electrical signal to the reception unit 16. The reception unit 16 generates a reception signal by phase-adding the electrical signals output from each transducer element such that the electrical signals based on the ultrasound waves received from a direction of the transmission beam are intensified, and outputs the reception signal to the information processing unit 34. A reception beam is formed in the ultrasound probe 12 through the phase-addition. Here, the reception beam refers to a directional pattern indicating a direction in which ultrasound waves, in which the reception signals are intensified, arrive. The reception signal corresponding to the reception beam is output from the reception unit 16 to the information processing unit 34 as a signal for generating B-mode image data. In the following description, the transmission beam and the reception beam are collectively referred to as a transmission/reception beam.

The information processing unit 34 comprises a B-mode image generation section 18, a state determination section 20, an image synthesis section 22, an image memory 24, and a display processing section 26 and configures an ultrasound image processing device that generates image data based on the reception signal. The information processing unit 34 may include a processor that realizes a function of each component by executing a program. In this case, the processor virtually configures each component (the B-mode image generation section 18, the state determination section 20, the image synthesis section 22, and the display processing section 26) by executing the program.

The reception signal output from the reception unit 16 is input to the B-mode image generation section 18. The B-mode image generation section 18 generates B-mode image data based on the reception signal obtained in a scanning direction of the transmission/reception beam.

The transmission unit 10, the ultrasound probe 12, and the reception unit 16 repeatedly scan the subject 14 with the transmission/reception beams. The B-mode image generation section 18 sequentially generates pieces of B-mode image data over time at a predetermined frame rate.

The display processing section 26 generates a video signal indicating B-mode images sequentially generated over time based on the pieces of B-mode image data sequentially generated over time, and outputs the video signal to the display 28. The display 28 displays an image based on the B-mode images sequentially generated over time, that is, a real-time B-mode image, based on the video signal.

The ultrasound diagnostic apparatus 100 also executes processing of displaying a panoramic image. In the panoramic image processing, the user manually transports the ultrasound probe 12 along a surface of the subject 14. In addition, a series of pieces of B-mode image data sequentially generated over time by the B-mode image generation section 18 are stored in the image memory 24. The B-mode image data stored in the image memory 24 is synthesis image data for generating panoramic image data.

The image memory 24 may store a maximum of N frames of pieces of B-mode image data. In this case, in a case where the B-mode images stored in the image memory 24 have reached N frames and a new B-mode image is generated, the oldest B-mode image data is deleted from the image memory 24, and then the new B-mode image is stored in the image memory 24.

The image synthesis section 22 generates panoramic image data based on the series of pieces of B-mode image data stored in the image memory 24 and outputs the panoramic image data to the display processing section 26. The display processing section 26 generates a video signal indicating a panoramic image based on the panoramic image data and outputs the video signal to the display 28. The display 28 displays the panoramic image based on the video signal.

Figure 2:
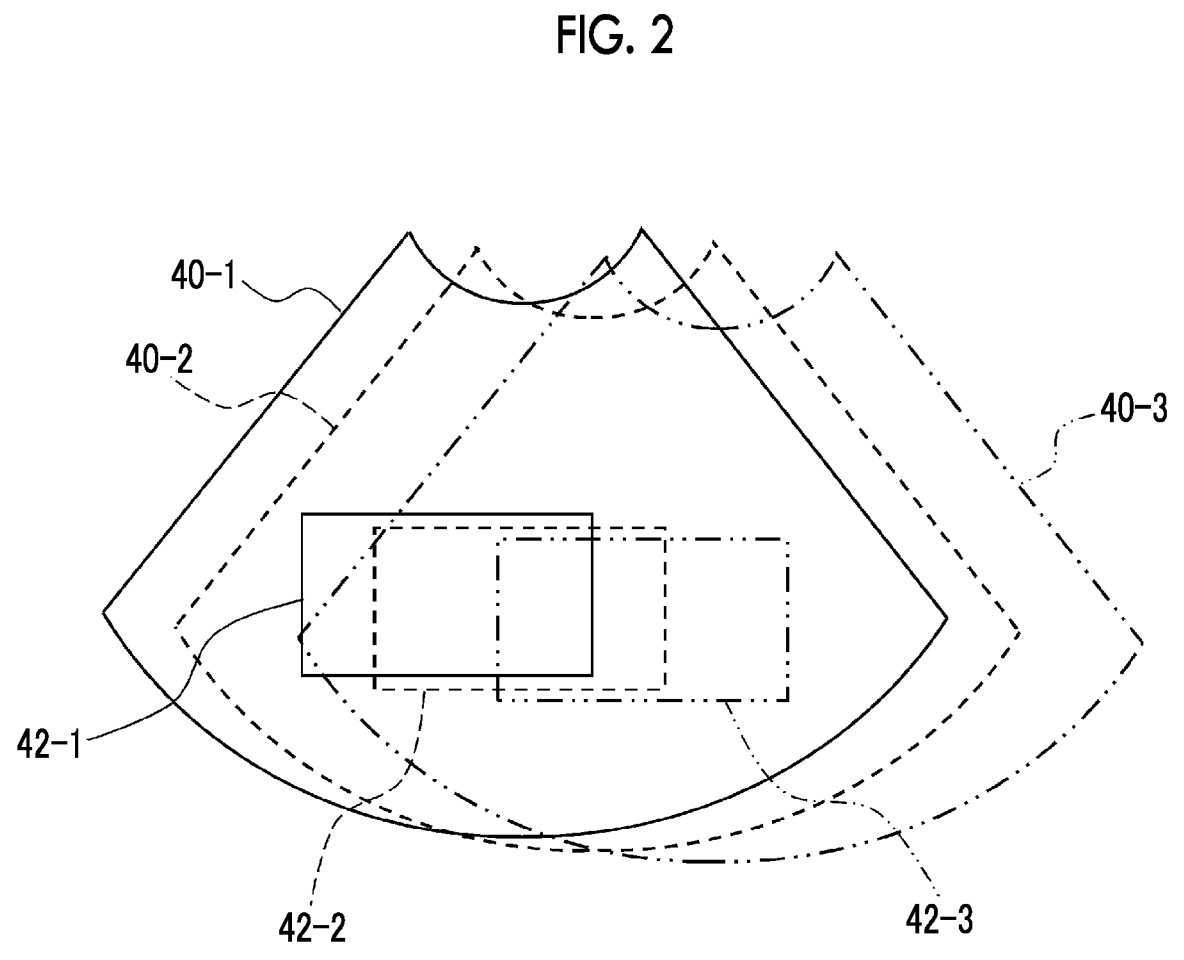

FIG. 2 conceptually shows the B-mode image acquired through the panoramic image processing. In order to simplify the description, three frames of B-mode images are shown. B-mode images 40-1 to 40-3 that are sequentially generated over time while the user transports the ultrasound probe 12 along the surface of the subject 14 are shown. The B-mode images 40-1 to 40-3 may be images based on pieces of B-mode image data generated at predetermined frame intervals and every predetermined number of frames with respect to the frame rate at which the B-mode image generation section 18 generates the B-mode image data.

A region of interest for displaying the panoramic image is set for each B-mode image by the user's operation through the operation unit 32. FIG. 2 shows region-of-interest images 42-1 to 42-3 for the B-mode images 40-1 to 40-3, respectively. A state in which the ultrasound probe 12 is transported to move a region, in which the B-mode image is acquired, and move the region-of-interest image is conceptually shown.

Figure 3:
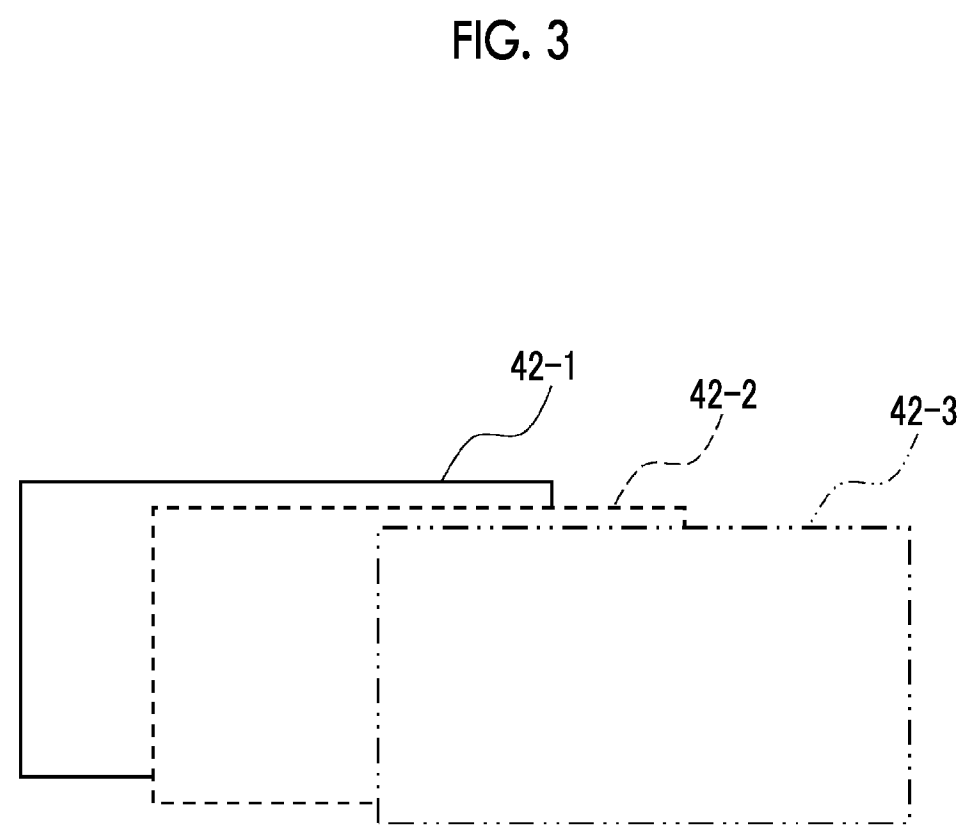

FIG. 3 shows a panoramic image acquired for the region of interest. In the present embodiment, for an overlapping portion of the region-of-interest image represented by the B-mode image data acquired earlier and the region-ofinterest image represented by the B-mode image data acquired later, the region-of-interest image represented by the B-mode image data acquired later is displayed. As a result, for a plurality of region-of-interest images (ultrasound images) that are sequentially generated over time and whose acquisition positions are different in the subject 14, a panoramic image is displayed as an image in which the region-of-interest image acquired later is superimposed on the region-of-interest image acquired earlier.

In the overlapping portion between the region-of-interest image acquired earlier and the region-of-interest image acquired later, a display position (the position in the image displayed on the display 28) of any one of two region-of-interest images in the overlapping portion may be adjusted by the image synthesis section 22 such that an approximation degree indicating a degree of approximation between the two region-of-interest images increases. The approximation degree between the two region-of-interest images in the overlapping portion may be a correlation value in the overlapping portion of the two region-of-interest images. In this case, for example, processing of obtaining a correlation value in the overlapping portion while moving a display position of at least one of the two region-of-interest images, and deciding on a display position of each region-of-interest image such that the correlation value is maximized is executed by the image synthesis section 22.

The panoramic image may be an image in which the region-of-interest image acquired earlier is displayed on the overlapping portion between the region-of-interest image acquired earlier and the region-of-interest image acquired later. That is, the panoramic image data represents, for the overlapping portion of the region-of-interest image based on the B-mode image data acquired earlier and the region-of-interest image based on the B-mode image data acquired later, either the region-of-interest image based on the B-mode image data acquired earlier or the region-of-interest image based on the B-mode image data acquired later.

A boundary image for naturally expressing the connection between the two region-of-interest images is disposed in transition regions within the overlapping portion between the region-of-interest image acquired earlier and the region-of-interest image acquired later. Here, the transition region refers to a region that extends a predetermined transition distance 8 into the overlapping portion from a boundary line between the region-of-interest image acquired earlier and the region-of-interest image acquired later. In a case where a radius of curvature of the boundary line is shorter than the transition distance $\delta$, a transition region is defined as a region that extends the transition distance & into the overlapping portion from every position of the boundary line.

Figure 4:
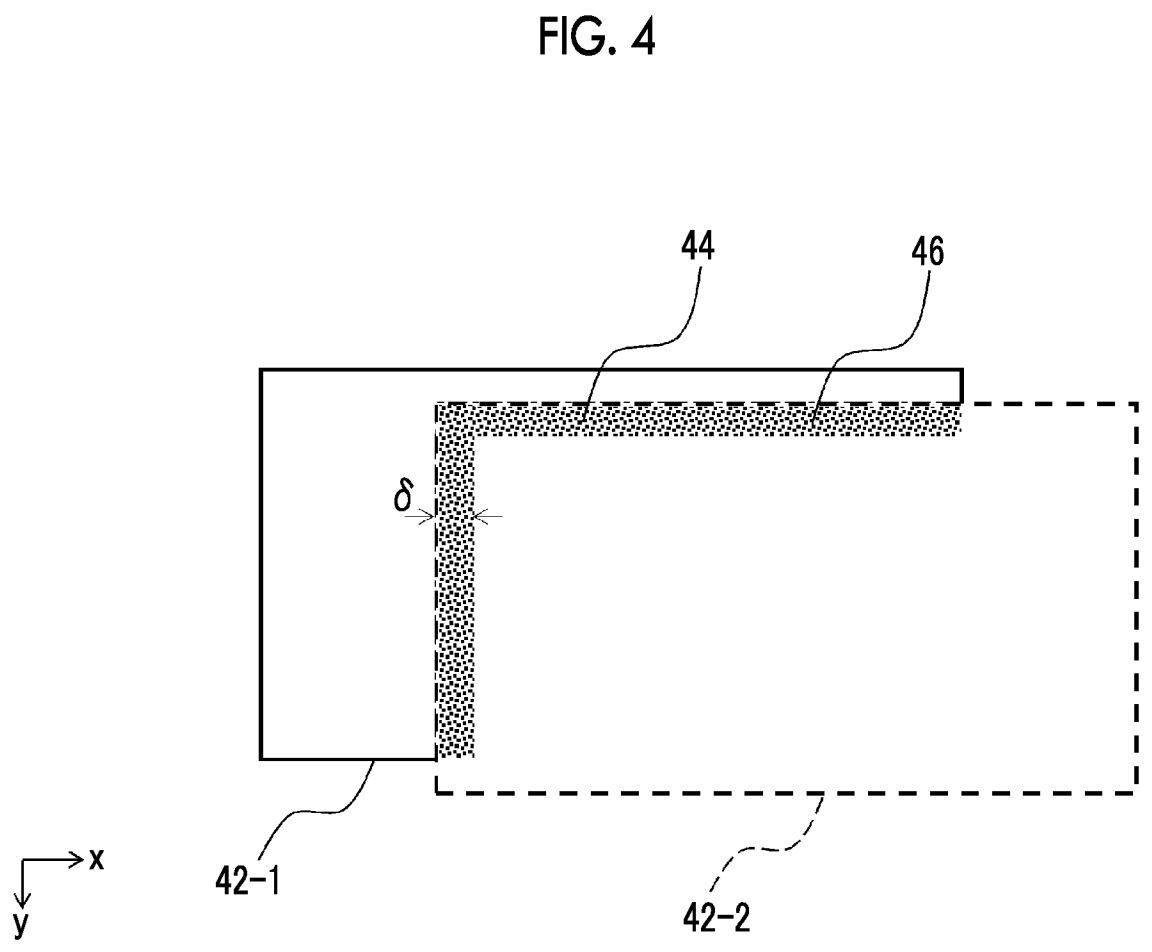

FIG. 4 shows the region-of-interest images 42-1 and 42-2 and a boundary image 46 disposed in these transition regions 44. The boundary image 46 may be a transparent image that allows one to see through the other. The image synthesis section 22 obtains a synthesis pixel value C by executing transparency processing represented by the following (Equation 1) for a pixel value A of each pixel in the transition region 44 of the region-of-interest image 42-1 and a pixel value B of each pixel in the region-of-interest image 42-2.

$$C = \alpha \cdot A + (1-\alpha) \cdot B \qquad \text{(Equation 1)}$$

Here, a transparency factor $\alpha$ indicates a degree to which the pixel value A of the region-of-interest image 42-1 contributes to the synthesis pixel value C of the transparent image. The value of the transparency factor $\alpha$ is decided on according to the position of the transition region 44. That is, the transparency factor $\alpha$ is a function related to the coordinate value (x, y) of a point P (x, y) on the transition region 44 and has a value of 0 or more and 1 or less. Note that the xy coordinate system is defined on a plane on which the panoramic image is formed. The transparency factor $\alpha$ may be decided on such that the value of the transparency factor $\alpha$ is 1 at the boundary line between the region-of-interest image 42-1 and the region-of-interest image 42-2 and approaches 0 from 1 as it moves from the boundary line toward the inside of the overlapping portion.

The image synthesis section 22 may execute processing of obtaining a correlation value between the region-of-interest images 42-1 and 42-2 in the transition regions 44 to dispose the transparent image in the transition regions 44 in a case where the correlation value exceeds a predetermined threshold value and to dispose a gap image with a predetermined aspect in a case where the correlation value is equal to or less than the predetermined threshold value. The gap image includes, for example, images with a predetermined color, a predetermined pattern, or a predetermined color and pattern. In addition, the image synthesis section 22 may execute processing of disposing the gap image as the boundary image 46 in the transition regions 44 regardless of the correlation value.

In this way, by disposing the transparent image or the gap image as the boundary image 46 in the transition regions 44 within the panoramic image, the following effects can be obtained. That is, even in a case where the transport direction of the ultrasound probe 12 changes abruptly due to factors such as a shake motion when the user transports the ultrasound probe 12 along the surface of the subject 14, a panoramic image that is easy to grasp as an overall view is formed.

In the panoramic image processing, the processing of sequentially generating and storing the pieces of B-mode image data may be temporarily ended, and then the image synthesis section 22 may generate the panoramic image data based on the series of pieces of B-mode image data. In this case, the panoramic image based on the pieces of B-mode image data stored in the image memory 24 when generation and storage of the B-mode image data have ended is displayed.

In addition, in the panoramic image processing, real-time panoramic image generation processing of updating the panoramic image data each time a predetermined number of frames, that is, F frames, of pieces of B-mode image data are newly generated may be executed. The image synthesis section 22 generates the panoramic image data based on the pieces of B-mode image data stored in the image memory 24 each time the B-mode image generation section 18 generates the F frames of pieces of B-mode image data. For example, the image synthesis section 22 reads out pieces of B-mode image data at F-frame intervals from the series of pieces of B-mode image data stored in the image memory 24 to generate panoramic image data.

(a) to (c) of FIG. 5 show examples of images displayed on the display 28 through the real-time panoramic image generation processing, respectively. The B-mode image is shown in the upper part, and the panoramic image is shown in the lower part. (a) of FIG. 5 shows an image to be displayed first. (b) of FIG. 5 shows an image to be displayed in a case where the pieces of B-mode image data representing the image of (a) of FIG. 5 are generated and then the F frames of pieces of B-mode image data are further generated. (c) of FIG. 5 shows an image to be displayed in a case where the pieces of B-mode image data representing the image of (b) of FIG. 5 are generated and then the F frames of pieces of B-mode image data are further generated. As shown in (a) to (c) of FIG. 5, the panoramic image is sequentially expanded by the newly generated region-of-interest images each time a time corresponding to the F frame elapses.

With the real-time panoramic image generation processing, the user can transport the ultrasound probe 12 along the subject 14 while checking the panoramic images that are sequentially updated. This facilitates an operation to transport the ultrasound probe 12 while adjusting the position of the ultrasound probe 12 such that an appropriate panoramic image is formed.

Processing of starting the acquisition of the B-mode image data as the synthesis image data and ending the acquisition of the B-mode image data as the synthesis image data, in response to the operation of the ultrasound probe 12 by the user, will be described. This processing is performed by determining the state of the ultrasound probe 12. That is, the acquisition of the synthesis image data is started in a case where it is detected that the ultrasound probe 12 has remained stationary for a predetermined time. Then, the acquisition of the synthesis image data is ended in a case where it is detected that the ultrasound probe 12 is in a non-transport state. Here, the non-transport state refers to a state in which the ultrasound probe 12 that has been transported along the surface of the subject 14 in order to acquire the panoramic image is not transported along the subject 14, such as the ultrasound probe 12 having remained stationary for a predetermined time, having been separated from the subject 14, and having undergone an abrupt change in transport direction.

The state of the ultrasound probe 12 is determined by the state determination section 20 shown in FIG. 1. The state determination section 20 determines the state of the ultrasound probe 12 based on the pieces of B-mode image data sequentially generated over time by the B-mode image generation section 18.

The state determination section 20 determines that the ultrasound probe 12 is in contact with the subject 14 in a case where the brightness of the B-mode image represented by the B-mode image data is within a predetermined range. The brightness of the B-mode image may be defined by statistical values such as an average, a median, and a mode of the pixel values of a plurality of pixels constituting the B-mode image. For example, the state determination section 20 determines that the ultrasound probe 12 is in contact with the subject 14 in a case where the brightness exceeds a predetermined threshold value. The state determination section 20 determines that the ultrasound probe 12 is not in contact with the subject 14 in a case where the brightness is equal to or less than the predetermined threshold value. The state determination section 20 determines that the ultrasound probe 12 is in contact with the subject 14, and then executes the following processing.

The state determination section 20 obtains, for example, an approximation degree between two pieces of B-mode image data generated adjacently on a time axis. The approximation degree may be represented by a correlation value between two B-mode images represented by the two pieces of B-mode image data.

The state determination section 20 determines that the ultrasound probe 12 is in a transport state in a case where the approximation degree between the two pieces of B-mode image data generated adjacently on the time axis is equal to or less than a predetermined threshold value, and there is a position where the approximation degree when a position of one of the two B-mode images represented by the two pieces of B-mode image data is changed is maximized.

In addition, in a case where the approximation degree exceeds a predetermined threshold value over a predetermined number of frames, the state determination section 20 determines that the ultrasound probe 12 has remained stationary.

In a case where the approximation degree is not maximized even when the position of one of the two B-mode images represented by the two pieces of B-mode image data generated adjacently on the time axis is changed, the state determination section 20 determines that the ultrasound probe 12 is in a singular state. The singular state includes a state in which the ultrasound probe 12 is separated from the subject 14, and a state in which the transport direction is abruptly changed. The stationary state and the singular state of the ultrasound probe 12 are included in the non-transport state in which the ultrasound probe 12 is not transported along the subject 14.

FIG. 6 shows a flowchart showing a first example of the panoramic image processing. In this processing example, a series of pieces of B-mode image data are stored in the image memory 24 after the time when the ultrasound probe 12 has remained stationary for a predetermined time and before the ultrasound probe 12 is transported and enters the non-transport state. After the series of pieces of B-mode image data are stored in the image memory 24, the image synthesis section 22 generates the panoramic image data.

The B-mode image generation section 18 generates the B-mode image data based on the reception signal output by the reception unit 16 (S101). The display processing section 26 displays the B-mode image on the display 28 based on the B-mode image data (S102).

The state determination section 20 determines whether or not the ultrasound probe 12 has remained stationary for a predetermined time (S103). In a case where the state determination section 20 determines that the ultrasound probe 12 is not stationary for a predetermined time, the processing to be executed by the ultrasound diagnostic apparatus 100 returns to step S101. In a case where the state determination section 20 determines that the ultrasound probe 12 has remained stationary for a predetermined time, the processing to be executed proceeds to steps S104 to S107, and processing for generating the panoramic image is executed.

The processing of steps S101 to S103 is repeated after the start of the processing and before the state determination section 20 determines that the ultrasound probe 12 has remained stationary. As a result, the B-mode image is displayed on the display 28 in real time.

The B-mode image generation section 18 generates the B-mode image data based on the reception signal output by the reception unit 16 (S104). The B-mode image data is stored in the image memory 24 (S105). The display processing section 26 displays the B-mode image on the display 28 (S106). The state determination section 20 determines whether or not the ultrasound probe 12 is in the non-transport state (S107). In a case where the state determination section 20 determines that the ultrasound probe 12 is not in the non-transport state, the processing to be executed by the ultrasound diagnostic apparatus 100 returns to the processing of step S104. In a case where the state determination section 20 determines that the ultrasound probe 12 is in the non-transport state, the generation and storage of the B-mode image data and the display of the B-mode image are temporarily stopped, and the processing to be executed by the ultrasound diagnostic apparatus 100 proceeds to step S108.

After an affirmative determination is made in the processing of step S107, the image synthesis section 22 generates the panoramic image data based on the B-mode image data stored in the image memory 24 automatically or in response to the user's operation through the operation unit 32 (S108). The display processing section 26 displays the panoramic image on the display 28 (S109). The B-mode image generation section 18 and the display processing section 26 may display the B-mode images (real-time B-mode images) that are sequentially generated over time on the display 28 together with the processing of S108 and S109.

As described above, the information processing unit 34 as the ultrasound image processing device determines the state of the ultrasound probe 12 based on the B-mode image data (image data) acquired by the ultrasound probe 12 (S103). The information processing unit 34 starts the acquisition of the B-mode image data as the synthesis image data according to the state of the ultrasound probe 12 and ends the acquisition of the B-mode image data as the synthesis image data according to the state of the ultrasound probe 12 (S104 to S107). The information processing unit 34 executes processing of generating the panoramic image data by synthesizing the pieces of B-mode image data (synthesis image data) sequentially acquired over time (S108).

Figure 7:
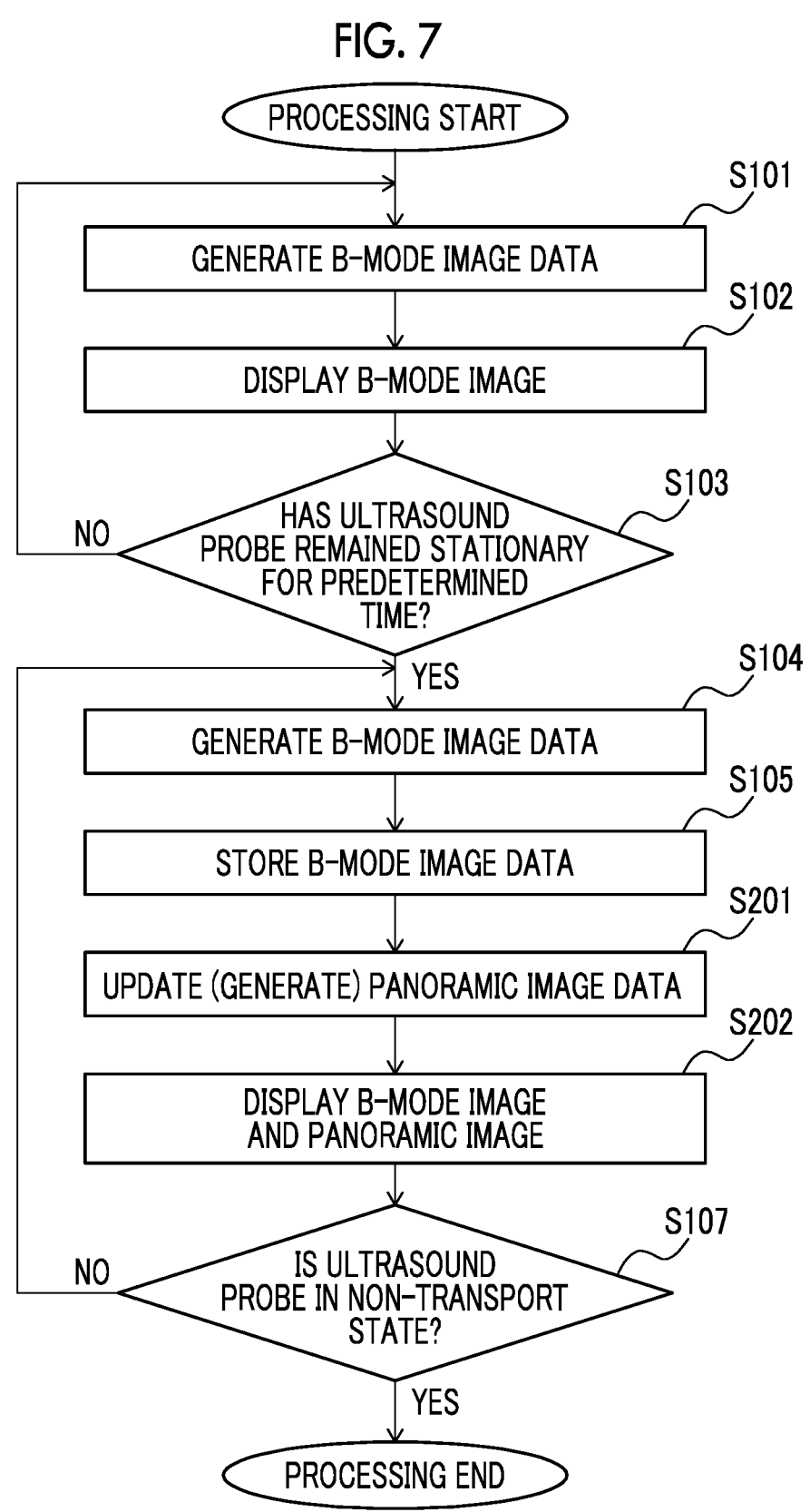
FIG. 7 is a flowchart showing a second example of the panoramic image processing.

FIG. 7 shows a flowchart showing a second example (an example of the real-time panoramic image generation processing) of the panoramic image processing. In this processing example, there is a difference from first example in that the image synthesis section 22 updates the panoramic image data (S201) each time the F frames of pieces of B-mode image data are generated and stored. Here, the update of the panoramic image data refers to processing of adding the region-of-interest image represented by the newly generated B-mode image data to the image based on the previously generated panoramic image data. In addition, there is a difference from the first example in that the updated panoramic image is displayed together with the B-mode image (S202).

In the processing of step S202 during a first loop in which steps S104 to S107 are repeated, the image synthesis section 22 generates the panoramic image data based on the initially generated B-mode image data. In this panoramic image data, a first single region-of-interest image is shown as the panoramic image. In the processing of step 202 in second and subsequent loops, the image synthesis section 22 updates the panoramic image data each time the F frames of pieces of B-mode image data are generated and stored.

For example, the image synthesis section 22 executes processing of increasing a count value by 1 each time the processing of S104 and S105 is executed for a single frame of B-mode image data. In a case where the count value reaches F, the image synthesis section 22 updates the panoramic image data and sets the count value to 0.

In this way, the information processing unit 34 executes the real-time panoramic image generation processing to sequentially update the panoramic image data each time a predetermined number of frames, that is, F frames, of pieces of B-mode image data as the synthesis image data are acquired (S201). The information processing unit 34 executes processing of sequentially displaying panoramic images based on the updated panoramic image data.

With the processing shown in FIG. 7, the panoramic image data is generated or updated each time the F frames of pieces of B-mode image data are generated while the ultrasound probe 12 is being transported along the subject 14. Then, as shown in FIG. 5, the panoramic image based on each piece of panoramic image data is displayed on the display 28.

As a result, the user can transport the ultrasound probe 12 along the subject 14 while checking the sequentially updated panoramic images. This facilitates an operation to transport the ultrasound probe 12 while adjusting the position of the ultrasound probe 12 such that an appropriate panoramic image is formed.

The configuration of the present disclosure is shown below.

Configuration 1

An ultrasound image processing device configured to execute:
  processing of determining a state of an ultrasound probe based on image data acquired by the ultrasound probe;
  processing of starting an acquisition of synthesis image data by the ultrasound probe according to the state of the ultrasound probe and ending the acquisition of the synthesis image data according to the state of the ultrasound probe; and
  processing of synthesizing pieces of synthesis image data sequentially acquired over time to generate panoramic image data.

Configuration 2

The ultrasound image processing device according to Configuration 1,
  in which the processing of generating the panoramic image data includes
    processing of sequentially updating the panoramic image data each time a predetermined number of frames of pieces of synthesis image data are acquired, and
  the ultrasound image processing device is configured to further execute
    processing of sequentially displaying panoramic images based on the updated panoramic image data.

Configuration 3

The ultrasound image processing device according to Configuration 1 or 2,
  in which the acquisition of the synthesis image data is started in a case where it is determined that the ultrasound probe is in a stationary state, and
  the acquisition of the synthesis image data is ended in a case where it is determined that the ultrasound probe is in a non-transport state.

Configuration 4

The ultrasound image processing device according to any one of Configurations 1 to 3,
  in which the panoramic image data represents,
    for an overlapping portion of an image represented by the synthesis image data acquired earlier and an image represented by the synthesis image data acquired later, either an image based on the synthesis image data acquired earlier or an image based on the synthesis image data acquired later.

Configuration 5

The ultrasound image processing device according to Configuration 4, in which the processing of generating the panoramic image data includes processing of disposing, within an overlapping portion of two ultrasound images represented by pieces of synthesis image data acquired adjacently on a time axis, a gap image with a predetermined aspect in transition regions of the two ultrasound images.

Configuration 6

The ultrasound image processing device according to Configuration 4, in which the processing of generating the panoramic image data includes processing of disposing, within an overlapping portion of two ultrasound images represented by pieces of synthesis image data acquired adjacently on a time axis, a transparent image that allows one to see through the other in transition regions of the two ultrasound images.

Configuration 7

The ultrasound image processing device according to Configuration 4, in which the processing of generating the panoramic image data includes processing of obtaining, within an overlapping portion of two ultrasound images represented by pieces of synthesis image data acquired adjacently on a time axis, an approximation degree for transition regions of the two ultrasound images, and processing of executing either one of processing of disposing a gap image with a predetermined aspect in the transition regions or processing of disposing a transparent image that allows one to see through the other in the transition regions, according to the approximation degree.

What is claimed is:

1. An ultrasound diagnostic apparatus, comprising:

an ultrasound probe;

a processor configured to:

start an acquisition of image data by the ultrasound probe;

start storing the image data acquired by the ultrasound probe in an image memory in response to the ultrasound probe having remained stationary for a predetermined time;

start generating panoramic image data by synthesizing the image data stored in the image memory after the storage of the image data is started;

determine whether the ultrasound probe is in a non-transport state based on image data acquired by the ultrasound probe after the storage of the image data is started, wherein the non-transport state refers to a state in which the ultrasound probe that has been transported along a surface of a subject scanned by the ultrasound probe is not transported along the subject; and end the generation of the panoramic image data in response to determining the ultrasound probe is in the non-transport state.

2. The ultrasound diagnostic apparatus according to claim 1, wherein the processor is configured to sequentially update the panoramic image data each time a predetermined number of frames of the image data are acquired, and sequentially display panoramic images based on the updated panoramic image data.

3. The ultrasound diagnostic apparatus according to claim 1, wherein the panoramic image data represents, for an overlapping portion of an image represented by the image data acquired earlier and an image represented by the image data acquired later, either an image based on the image data acquired earlier or an image based on the image data acquired later.

4. The ultrasound diagnostic apparatus according to claim 3, wherein the processor is configured to dispose, within an overlapping portion of two ultrasound images represented by the image data acquired adjacently on a time axis, a gap image with a predetermined color, a predetermined pattern, or a predetermined color and pattern in transition regions of the two ultrasound images, wherein the transition regions are regions that extends a transition distance into the overlapping portion from every position of a boundary line of the overlapping portion.

5. The ultrasound diagnostic apparatus according to claim 3, wherein the processor is configured to dispose, within an overlapping portion of two ultrasound images represented by the image data acquired adjacently on a time axis, a transparent image that allows one to see through the other in transition regions of the two ultrasound images, wherein the transition regions are regions that extends a transition distance into the overlapping portion from every position of a boundary line of the overlapping portion.

6. The ultrasound diagnostic apparatus according to claim 3, wherein the processor is configured to obtain, within an overlapping portion of two ultrasound images represented by the image data acquired adjacently on a time axis, an approximation degree for transition regions of the two ultrasound images, wherein the transition regions are regions that extends a transition distance into the overlapping portion from every position of a boundary line of the overlapping portion, and dispose a gap image in the transition regions in a case where the correlation value exceeds a predetermined threshold value and dispose a transparent image in the transition regions in a case where the correlation value is equal to or less than the predetermined threshold value.

* * * * *